(12) United States Patent
Reis et al.

(10) Patent No.: US 12,216,032 B2
(45) Date of Patent: Feb. 4, 2025

(54) DEVICE AND METHOD FOR THE DISSOCIATION OF TISSUE

(71) Applicant: Fraunhofer-Gesellschaft zur Förderung der angewandten Forschung e.V., Munich (DE)

(72) Inventors: Christian Reis, Römerberg (DE); Stefan Scheuermann, Mannheim (DE); Armin Schäfer, Mannheim (DE); Daniel Edinger, Spechbach (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1200 days.

(21) Appl. No.: 15/733,424

(22) PCT Filed: Jan. 24, 2018

(86) PCT No.: PCT/EP2018/051701
§ 371 (c)(1),
(2) Date: Sep. 29, 2020

(87) PCT Pub. No.: WO2019/145029
PCT Pub. Date: Aug. 1, 2019

(65) Prior Publication Data
US 2021/0140856 A1    May 13, 2021

(51) Int. Cl.
*G01N 1/00* (2006.01)
*B02C 18/06* (2006.01)
(Continued)

(52) U.S. Cl.
CPC ........... *G01N 1/286* (2013.01); *B02C 18/062* (2013.01); *B02C 18/10* (2013.01);
(Continued)

(58) Field of Classification Search
None
See application file for complete search history.

(56) References Cited

U.S. PATENT DOCUMENTS 6,358,474 B1    3/2002 Dobler et al.

FOREIGN PATENT DOCUMENTS

| DE | 102016216345 B3 | | 1/2018 |
| EP | 2540394 | * | 1/2013 |

(Continued)

OTHER PUBLICATIONS

"International Application Serial No. PCT/EP2018/051701, International Search Report mailed Oct. 15, 2018", (Oct. 15, 2018), 3 pgs.

(Continued)

*Primary Examiner* — Jyoti Nagpaul
(74) *Attorney, Agent, or Firm* — Schwegman Lundberg & Woessner, P.A.

(57) ABSTRACT

The invention relates to a device and a method for the dissociation of tissue. In one embodiment, the device has at least one dissociation unit, for receiving a tissue sample, which is disposed at least partially in a pot-shaped cell strainer. In addition, the invention relates, in one embodiment, to a device and a method for the dissociation of tissue, the tissue being dissociated by a grinder having mutually movable rows of teeth which cut the tissue when moving past each other in the one direction and grind the tissue when moving past each other in the opposite direction.

28 Claims, 5 Drawing Sheets

Figure 1:
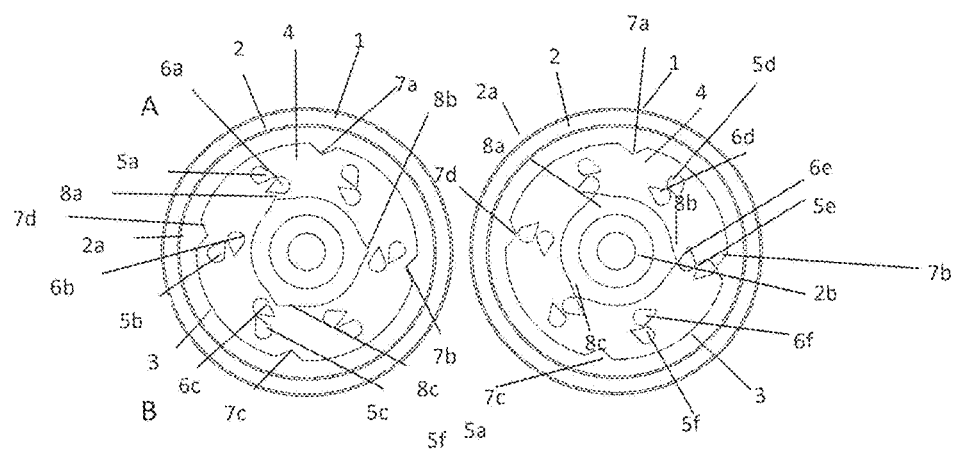

(51) Int. Cl.
  *B02C 18/10* (2006.01)
  *B02C 19/00* (2006.01)
  *C12M 3/08* (2006.01)
  *G01N 1/28* (2006.01)
  *G01N 1/40* (2006.01)

(52) U.S. Cl.
  CPC ........... *B02C 19/0056* (2013.01); *C12M 3/08* (2013.01); *G01N 1/4077* (2013.01); *G01N 2001/2866* (2013.01); *G01N 2001/4088* (2013.01)

(56) References Cited

FOREIGN PATENT DOCUMENTS

| EP | 2540394 A1 | 1/2013 |
|----|------------|--------|
| WO | WO-9509051 A1 | 4/1995 |
| WO | WO-2013070899 A1 | 5/2013 |
| WO | WO-2016097960 A2 | 6/2016 |

OTHER PUBLICATIONS

"International Application Serial No. PCT/EP2018/051701, Written Opinion mailed Oct. 15, 2018", (Oct. 15, 2018), 6 pgs.

* cited by examiner

DEVICE AND METHOD FOR THE DISSOCIATION OF TISSUE

PRIORITY APPLICATIONS

This application is a U.S. National Stage Filing under 35 U.S.C. § 371 from International Application No. PCT/EP2019/051387, filed on Jul. 21, 2019, and published as WO2019/141847 on Jul. 25, 2019, which claims the benefit of priority to German Application No. 10 2018 200 895.7, filed on Jul. 19, 2018; the benefit of priority of each of which is hereby claimed herein, and which applications and publication are hereby incorporated herein by reference in their entirety.

The invention relates to a device and a method for the dissociation of tissue. In one embodiment, the device has at least one dissociation unit, for receiving a tissue sample, which is disposed at least partially in a pot-shaped cell strainer. In addition, the invention relates, in one embodiment, to a device and a method for the dissociation of tissue, the tissue being dissociated by a grinder having mutually movable rows of teeth which cut the tissue when moving past each other in the one direction and grind the tissue when moving past each other in the opposite direction.

The dissociation of human or animal tissue represents a challenge for several reasons. Not only do tissues of a different origin differ in their consistency, also one and the same tissue sample can be composed very heterogeneously. Therefore, there has been no success to date in developing one method with which any type of tissue can be dissociated.

There are a few commercially available systems with which tissue and cells can be desintegrated. A reliable method for tissue dissociation into a single-cell suspension exists only with qualifications.

It is the object of the present invention to indicate a device and a method for the dissociation of tissue with which any type of tissue can be dissociated and preferably can be processed to form a single-cell suspension.

The object is achieved by the devices for the dissociation of tissue according to claim 1 and claim 6 and also by the method for the dissociation of tissue according to claim 24. The respective dependent claims indicate advantageous developments of the devices for the dissociation of tissue and of the method for the dissociation of tissue.

According to the invention, a device for the dissociation of tissue is provided, which has at least one dissociation unit for receiving a tissue sample and also a pot-shaped cell strainer. The at least one dissociation unit is thereby disposed at least partially in the pot-shaped cell strainer.

There should thereby understood by dissociation unit, a device with which tissue can be dissociated. The dissociation can thereby comprise in particular a cell desintegration and/or a tissue dissociation. In particular, the process of dissociation of tissue can comprise advantageously the grinding of tissue and/or the production of a single-cell suspension and/or the isolation of molecules.

According to the invention, the device for the dissociation of tissue, in this embodiment, has a pot-shaped cell strainer. There should thereby be understood by a pot-shape, in the most general sense, a concave shape in which the dissociation unit can be introduced at least partially. In particular, there can be understood by a pot-shape, advantageously a cylindrical shape with an end-face or front-face which is open on one side. The term "cylindrical shape" can thereby be understood in the most general mathematical sense and comprise a cylinder with any base area, the cylindrical shape preferably having a straight cylindrical axis. Advantageously, the cylindrical shape has however a circular base area so that there can be understood by a cylindrical shape, in the sense of the invention, advantageously a circular-cylindrical shape with end-face or front-face which is open on one side.

If the cell strainer is circular-cylindrical in this sense, then also the dissociation unit advantageously has a circular cross-section. Then the dissociation unit with an axis perpendicular to the circular cross-section in the centre thereof, can be disposed coaxially to a cylindrical axis of the circular-cylindrical cell strainer at least partially in the ceil strainer.

Preferably, the dissociation unit in the cell strainer is protected against rotation relative to the cell strainer.

The cell strainer advantageously has at least one area which acts as strainer for the tissue components produced by the dissociation unit. A mesh width of the strainer can thereby be chosen suitably as a function of the tissue components produced by the dissociation, A cell strainer which has a circular-cylindrical pot-shape with an open and a closed end-face or front-face is particularly advantageous, the closed end-face or front-face and the jacket-face being formed by corresponding strainers. The strainers can thereby be supported advantageously by a frame. The frame can thereby specify the outer shape of the cell strainer. If the cell strainer has a cylindrical shape, then the frame extends advantageously along edges of the cylinder shape, the portions of the frame extending along the edges of the cylindrical shape being able to be connected to each other particularly preferably by struts which can extend particularly preferably parallel to the cylindrical axis. This shape of frame is advantageous both for circular-cylindrical strainers and for cylindrical strainers with different base areas. The frame can thereby be produced advantageously from plastic material.

In an advantageous embodiment of the invention, the device for the dissociation of tissue can have at least one vessel for receiving a tissue sample. The vessel can thereby be a component of the dissociation unit.

A grinder, with which the tissue sample can be dissociated is advantageously disposed in the vessel. The feature can thereby advantageously have at least two mutually movable rows of teeth which have respectively a plurality of teeth. The grinder can therefore have at least one first row of teeth with a plurality of teeth and at least one second row of teeth with a plurality of teeth. Advantageously, adjacent rows of teeth can be disposed at such a spacing relative to each other that the teeth of these respectively adjacent rows of teeth effect a dissociation of a part of the tissue sample in a spacing region by their minimum spacing relative to each other. Advantageously, the at least one first row of teeth can therefore be movable relative to the at least one second row of teeth so that the teeth of the respectively first row of teeth move past the teeth of the respectively second row of teeth. Then respectively one of the at least one first rows of teeth and one of the at least one second rows of teeth can be disposed at such a spacing adjacent to each other that the teeth of these respectively adjacent rows of teeth, if they are moved past each other, effect a dissociation of a part of the tissue sample in a spacing region by their minimum spacing relative to each other.

Advantageously, the vessel can have a base and a cover. The base and the cover can thereby be configured such that they form or compose the vessel together. However it is also possible that base and jacket cover opposite sides of a cylindrical jacket so that base, cover and jacket together form the vessel. In an advantageous embodiment, the vessel can be cylindrical, particularly preferably circular-cylindrical. Then the rows of teeth are disposed, particularly preferably, concentrically about a cylindrical axis of the vessel.

In an advantageous embodiment of the invention, the teeth of the rows of teeth can be configured such that, if they move past each other in one direction, they cut the part of the tissue sample and, if they move past each other in the direction opposite to this direction, they grind the part of the tissue sample.

The term "grinder" can comprise both devices for cutting and for grinding. Alternatively to the term "grinder" therefore the term "comminution unit" can also be used.

Advantageously, the grinder can have at least two mutually movable rows of teeth. Each of the rows of teeth then has a plurality of teeth. The term "row of teeth" is intended hereby to describe in general a quantity of teeth which move in common in the comminution process. The teeth of one row of teeth can advantageously be disposed along a line which can have various shapes. The teeth of one row of teeth can be disposed respectively, particularly advantageously, along a circularly closed line.

Advantageously, adjacent rows of teeth are disposed at such a spacing relative to each other that the teeth of these respectively adjacent rows of teeth effect a dissociation of a part of the tissue sample in a spacing region by their minimum spacing relative to each other. The spacing of two rows of teeth can hereby be defined either as a spacing of the lines along which the teeth of one row of teeth are disposed or as a spacing of the teeth at the point of their respectively greatest proximity. If the teeth of two adjacent rows of teeth have different spacings in their respectively greatest proximity, then, as spacing, also an average spacing of the teeth, measured at the point of the greatest proximity respectively of two teeth, can be defined.

The spacing between the rows of teeth is advantageously dimensioned such that the teeth, when moving past each other, effect a dissociation of a part of the tissue sample. The respectively dissociated part of the tissue sample is thereby that part on which the two teeth moving past each other have a comminuting effect. The dissociation thereby takes place in a spacing region of the teeth from each other by the minimum spacing of the teeth from each other. When moving past each other, therefore respectively two teeth of the adjacent rows of teeth approach each other, begin, from a specific spacing, an effect on the tissue for the dissociation of the tissue which exists until the teeth, after they have passed each other, have a specific maximum spacing from each other.

Reference may be made here to the fact that the teeth of the adjacent rows of teeth need not be assigned in pairs relative to each other. Advantageously, rather it is the case that the teeth of the adjacent rows of teeth pass each other in succession.

Advantageously, the teeth are configured such that they cut the tissue if they move past each other in one direction and grind the tissue if they move past each other in the opposite direction. In order to achieve this effect, the teeth can have a large number of different shapes. Advantageously, the teeth can have a blade on one side in the direction of movement and, on their opposite side in their direction of movement, a part of a grinding or crushing device so that two teeth of adjacent rows of teeth which come together with this side effect grinding of the tissue.

In two respectively adjacent rows of teeth, which together effect a dissociation of the tissue, the cutting edges and the grinding edges of the two rows of teeth are thereby advantageously orientated opposite each other. If the two rows of teeth move past each other in the opposite direction, then they effect cutting in the one direction with the two cutting edges and, in the opposite direction, grinding with the grinding sides. In general, a cutting direction and a grinding direction, which are respectively opposite for cooperating adjacent rows of teeth, can be defined, i.e. the cutting directions of the adjacent rows of teeth are opposite each other and the grinding directions of the adjacent rows of teeth are opposite each other.

For other applications, the teeth can also have other cross-sections, such as for example cylindrical, or have a diamond-shaped, parallelogram-shaped or rhomboid base.

In an advantageous embodiment, the rows of teeth are configured to be circular and concentric to each other. This means that the teeth of one row of teeth are respectively lined up along a circle and these circles are concentric to each other. The described cutting direction and the described grinding direction are then advantageously tangential or parallel to the corresponding circular lines.

In an advantageous embodiment of the invention, the device for the dissociation of tissue can in addition have a reagent vessel in the opening of which the dissociation unit and/or the vessel for receiving the tissue sample can be disposed. The reagent vessel can thereby be e.g. a glass vessel or a plastic material vessel or be produced from other suitable materials. Advantageously, the reagent vessel can have a cylindrical portion, the length of which is longer in the direction of its cylindrical axis than a diameter of the reagent vessel. The cylindrical shape can have the opening on a side in which the dissociation unit and/or the vessel can be disposed.

In an advantageous embodiment of the invention, the rows of teeth disposed in the cover of the vessel can be movable relative to the reagent vessel and the rows of teeth disposed in the base of the vessel can be fixed relative to the reagent vessel. In the normal case, the vessel will be insertable in the opening of the reagent vessel and be able to be screwed together there for example. In this embodiment, the rows of teeth which are fixed relative to the reagent vessel should therefore be fixed in the state in which the vessel is disposed in the reagent vessel for use as intended. The movability of the teeth disposed in the cover can be effected then by suitable design of the vessel.

In an advantageous embodiment of the invention, the components of the grinder, i.e. the rows of teeth, can be configured as exchangeable inserts. These inserts can be insertable into the vessel. The rows of teeth can thereby be disposed on two plates so that the teeth are disposed between the plates in a common plane.

The idea according to the invention can also be achieved by a device which has at least one vessel for receiving a tissue sample, and also a grinder disposed in the vessel, the grinder having at least two mutually movable rows of teeth. For the vessel, the grinder and the rows of teeth, what was mentioned above can likewise advantageously be relevant.

In this embodiment of the invention, each of the rows of teeth can have a plurality of teeth, those adjacent ones of the rows of teeth being disposed at such a spacing relative to each other that the teeth of these respectively adjacent rows of teeth effect a dissociation of a part of the tissue sample in a spacing region by their minimum spacing relative to each other, the teeth being configured such that, if they move past each other in one direction, they cut the part of the tissue sample and, if they move past each other in the opposite direction, they grind the part of the tissue sample. Reference may be made to the fact that, in this embodiment of the invention, the pot-shaped cell strainer is not essential. The mentioned dissociation unit can advantageously be the grinder in this embodiment.

Also in this embodiment, the device can have a reagent vessel in the opening of which the mentioned vessel and the grinder can be disposed. Then the rows of teeth disposed in the cover of the vessel can also be movable here relative to the reagent vessel and the rows of teeth disposed in the base of the vessel can be fixed relative to the reagent vessel. What was said above relating to the reagent vessel can apply here correspondingly.

The following statements can apply advantageously for all embodiments of the invention.

In an advantageous embodiment, possibly the cell strainer and/or the dissociation unit and/or the vessel and/or the grinder can be disposed at least partially inside a closing cap of the reagent vessel. Advantageously, the closing cap can then surround the opening of the reagent vessel. The cell strainer, the dissociation unit, the vessel and/or the grinder can hereby be disposed, as described above, in the opening of the reagent vessel. If the closing cap surrounds the opening of the reagent vessel, then the corresponding elements can be disposed at the same time at least partially inside the closing cap. The fact that the closing cap surrounds the opening of the reagent vessel can mean in particular that the closing cap encloses or encompasses the opening. The cell strainer, the dissociation unit, the vessel and/or the grinder can particularly advantageously be fixed on the closing cap or be clamped or jammed by means of the closing cap between an edge of the reagent vessel and the closing cap. For this purpose, the corresponding element can have for example an edge which extends along an outer circumference of the corresponding element, and which, if the closing cap is screwed onto the reagent vessel, sits on the edge of the reagent vessel and is pressed by the closing cap against this edge.

In all embodiments of the invention, possibly the rows of teeth can extend circularly and concentrically to each other. The rows of teeth can extend in a common plane and be movable mutually in this plane particularly advantageously.

Preferably, the rows of teeth extend in a common plane and are movable mutually in this plane. Preferably, this plane is parallel to a base surface of the vessel and/or to a cover surface of the vessel. In this way, half of the rows of teeth can be disposed on the base of the vessel and the other half of the rows of teeth on a cover of the vessel. The teeth disposed on the base therefore protrude from the base into the vessel and the teeth disposed on the cover protrude from the cover into the vessel. Advantageously, the teeth can have respectively a general cylindrical shape, i.e. a shape which is defined by suitably shaped side surfaces which extend parallel to a straight line which is perpendicular to the row of teeth. In a cross-section perpendicular to this straight line, the teeth can respectively have the described shape with which they cut in one direction and grind in the opposite direction.

Advantageously, the teeth respectively have a cross-section in a plane perpendicular to their cylindrical axis or in a plane parallel to the common plane in which the rows of teeth extend, which have a pointed corner and a rounded side opposite the acute corner. The pointed corner and the rounded side are thereby situated opposite each other preferably in the direction of movement of the rows of teeth. The teeth therefore have preferably a drop shape in their cross-section. Advantageously, the pointed corners of teeth of adjacent rows of teeth are thereby directed in opposite directions and hence also the round corners.

In an advantageous embodiment, of the invention, those edges of the cross-section of the teeth which connect the tip to the rounded side are curved in the direction of a line along which the row of teeth extends to which the corresponding tooth belongs. This means that the corresponding sides are curved in the same direction as the line along which the row of teeth extends. In an advantageous embodiment, the radius of curvature of one of these two sides can thereby be essentially equal to the radius of curvature of the line along which the row of teeth extends.

The drop shape can thereby advantageously be understood as a parallelogram in which one of the two triangles separated by a short diagonal of the parallelogram is replaced by a circular arc which abuts, at the obtuse singles of the parallelogram, on the other of the two triangles. The circular arc here forms the rounded side and the remaining acute angle the pointed corner. Advantageously, the drop form is then mirror-symmetrical about the long diagonal of the original parallelogram, i.e. the axis of the tip to the furthest away point on the round corner. The radius of the circular arc can thereby be situated on the short diagonal of the original triangle. The circular arc can optionally be exactly a semicircle so that the centre of the circular arc is situated on the short diagonal of the original triangle. Alternatively, the circular arc can also abut on the straight sides, such that the straight sides are situated tangentially on the circular arc. In this case, the centre is situated somewhat further away from the tip.

The above-described drop form can be optionally bent also along the long diagonal of the parallelogram. The mirror symmetry is then lost and the shape is more similar to a fin.

Advantageously, the vessel can enclose a circular-cylindrical volume. The rows of teeth can then surround the cylindrical axis coaxially.

Advantageously, the side wall of the vessel delimiting the cylindrical volume can have one or more projections in the direction of the rows of teeth, that the row of teeth situated closest to the side wall having such a spacing from this side wall that the teeth of this closest row of teeth effect a dissociation of a part of the tissue sample in cooperation with the projections. Advantageously, the projections effect, with the teeth of the row of teeth nearest them, grinding of a part of the tissue sample. The projections can for example have a triangular shape in a sectional plane perpendicular to the cylindrical axis of the vessel.

In an advantageous embodiment, the vessel and/or the cover can have a base element which is surrounded by rows of teeth. The base element can have one or more projections in the direction of the rows of teeth, that row of teeth closest to the base element having such a spacing from this base element that the teeth of this closest row of teeth effect a dissociation of a part of the tissue sample in a spacing region about their minimum spacing from the projections. Advantageously, the vessel is also configured here such that it surrounds a cylindrical interior. The base element can thereby be configured likewise to be cylindrical with a cylindrical axis which is coaxial to the cylindrical axis of the vessel. The rows of teeth can then surround the base element circularly with the cylindrical axis as centre.

In an advantageous embodiment of the invention, a diameter of the vessel, in that plane in which the rows of teeth extend, can be greater than or equal to 0.5 cm, preferably greater than or equal to 1 cm, preferably greater than or equal to 2 cm and/or less than or equal to 4 cm, preferably less than or equal to 3 cm.

Preferably, a minimum spacing of teeth of adjacent rows of teeth, in the state of greatest proximity, can be respectively greater than or equal to 50 µm, preferably greater than or equal to 100 µm, preferably greater than or equal to 200 µm and/or less than or equal to 500 µm, preferably less than or equal to 400 µm, preferably less than or equal to 300 µm. The minimum spacing described here should be understood such that, when the teeth of adjacent and cooperating rows of teeth move past each other, the teeth move towards each other, then they reach the minimum spacing and subsequently move away from each other. The minimum spacing should thereby be the spacing, between two points of the profiles of the teeth which are moving past each other, which has the lowest value.

In an advantageous embodiment of the invention, the housing can have a base and a cover, one half of the rows of teeth being able to be disposed on the base and the other half of the rows of teeth being able to be disposed on the cover. Advantageously, the rows of teeth disposed on the cover can respectively be adjacent to the rows of teeth disposed on the base in a plane in which the rows of teeth extend. Particularly preferably, respectively one row of teeth disposed on the cover cooperates with one row of teeth disposed on the base for the tissue dissociation.

According to the invention, adjacent rows of teeth can be mutually movable. For this purpose, half of the rows of teeth can be disposed fixed relative to the housing and the other half of the rows of teeth, which respectively cooperate with the rows of teeth which are disposed fixed for the dissociation, can be movable relative to the housing. In an advantageous embodiment of the invention, the movable rows of teeth can be disposed on the cover. For this purpose, the cover can advantageously be movable. Alternatively, the cover can be fixed relative to the housing, and the rows of teeth can be configured movably relative to the cover and hence also relative to the housing. For this purpose, suitable mechanics can be integrated in the cover which are actuatable particularly preferably from outside the housing if the latter is closed by the cover.

In an advantageous embodiment of the invention, the mentioned closing cap of the reagent vessel can have an opening in its centre. In addition, the cover of the vessel can advantageously have an opening which is coaxial to the opening in the closing cap so that the opening of the closing cap and of the vessel are continuous. Then the openings in the closing cap and in the cover can be configured such that a driveshaft can actuate the cover of the dissociation unit or of the vessel for moving the teeth of the at least one second row of teeth or of the at least one row of teeth disposed on the cover relative to the teeth of the at least one first row of teeth or the at least one row of teeth disposed on the base. The driveshaft can engage, for this purpose, through the opening in the closing cap into the opening in the cover of the vessel.

In an advantageous embodiment of the invention, the cover of the housing or of the dissociation unit can also have a magnetic element, by means of which the at least one row of teeth is actuatable by means of a magnet. In this case, an opening in the closing cap is not required but can be provided nevertheless, for example in order to be able to introduce substances into the housing.

Advantageously, the opening in the closing cap and/or the opening in the cover of the vessel can have a septum, through which liquid can be introduced into the dissociation unit, the vessel and/or the reagent vessel. Advantageously, such a septum can be accommodated at one end of the opening, orientated towards the reagent vessel, in the cover of the vessel so that a driveshaft can engage through the closing cap and the opening of the cover in the opening in the cover without being impeded by the septum. If, as described above, the closing cap and the cover respectively have an opening, then it is particularly advantageous if the opening in the closing cap is sealed relative to the opening in the cover.

In an advantageous embodiment of the invention, the cell strainer and/or the base of the vessel can have elements, by means of which a relative movement of the base relative to the cell strainer, e.g. during actuation of the cover by means of a motor, can be prevented.

Reference may be made to the fact that, according to the invention, the vessel can be liquid-impermeable. However, it is also possible that the vessel is permeable for liquids, such as for example the ceil suspension. This is advantageous in particular if the device according to the invention, as described above, has a reagent vessel and/or a cell strainer. It is then possible firstly to undertake a tissue dissociation by means of the dissociation unit or the grinder and subsequently to further process this, for example to centrifuge or to clean this, in the reagent vessel and/or in the cell strainer. After the end of the desintegration process, the cell suspension can be separated for example by means of centrifugation of tissue residues. Then in the reagent vessel, which can be for example a centrifugal tube, the cell suspension can be collected. It is advantageous here that from introducing the tissue sample via the desintegration to further processing and analysis the system can remain closed, as a result of which the danger of contamination can be significantly reduced and, at the same time, user friendliness is increased.

The mentioned rows of teeth can be integrated fixed in the cover and in the base. It is however also possible to configure the rows of teeth in the cover and/or in the base of the vessel as exchangeable inserts. In particular, such an exchangeable insert in the cover can be mounted movably relative to the cover so that it is actuatable for movement of the teeth. The grinder can therefore have for example two inserts with respectively one or more rows of teeth which engage in each other and rotate in opposite directions.

In an advantageous embodiment of the invention, also the dissociation unit can be formed by disposing an insert with at least one row of teeth on the closing cap of the reagent vessel and inserting an insert with at least one row of teeth into the cell strainer or integrating it fixed into the latter. In this embodiment of the invention, the two inserts can be regarded together as housing in the above-described sense or form such a housing.

Advantageously, one of the inserts can have a jacket surrounding the rows of teeth concentrically to their course, which jacket can act as outer wall of the housing. Then the other insert with the rows of teeth disposed on the base of the housing can be placed on the cover. The base can then sit on an edge of the mentioned jacket face and advantageously be mounted to slide relative to the latter.

In an advantageous embodiment of the invention, the vessel, for receiving the tissue sample, can therefore have, on the one hand, the cover with the at least one second row of teeth and, on the other hand, the base with the at least one first row of teeth. The at least one second row of teeth can therefore be disposed on an end-face of the cover and a jacket can surround the end-face at its edge. Particularly advantageously, the jacket face is thereby a cylindrical face which is concentric to an axis about which the teeth of the at least one second row of teeth extend. The base can then have a plate which can also have openings on which the at least one first row of teeth is disposed. In the assembled state, the plate of the base can sit on that edge of the jacket face of the cover which is situated opposite the end-face of the cover.

The thus formed vessel can advantageously be disposed at least partially in the closing cap of the reagent vessel and, particularly preferably, can be screwed in the opening of the reagent vessel with the closing cap.

According to the invention, in addition a method for the dissociation of tissue is described, which is implementable with a device as described above. A tissue sample is thereby introduced into the corresponding device and then the dissociation unit or the grinder is actuated. Advantageously, if necessary, the at least two rows of teeth which are mutually movable are moved relative to each other.

If the device is configured such that the tissue sample is cut in one direction and ground in the other, advantageously the rows of teeth are moved mutually both in the cutting direction and in the grinding direction in the method according to the invention.

Advantageously, the rows of teeth can be moved relative to each other at a speed of rotation of greater than or equal to 60 rpm, preferably greater than or equal to 200 rpm, preferably greater than or equal to 300 rpm and/or less than or equal to 700 rpm, preferably less than or equal to 500 rpm, particularly preferably less them or equal to 400 rpm.

In an advantageous embodiment of the invention, the rows of teeth, whilst they are moved relative to each other, are moved periodically in the direction perpendicular to the direction of this movement. The periodic movement can therefore be effected in the direction of the cylindrical axis of the vessel or the axis of rotation of the rows of teeth.

Preferably, the tissue is provided with a liquid, such as for example a medium, or enzyme solution. By means of rotation in both directions and optionally a linear movement up and down of the grinding cylinder, the tissue can be processed.

Optionally, the grinder can be operated also uncoupled from the cover or housing, for example by a magnetic drive. In this case, the plate bearing a part of the teeth can be moved with an external magnet. The corresponding plate can have magnetic material for this purpose.

According to the type of tissue, the comminution method can be advantageously implemented between 30 seconds and 10 minutes with one or more changes of direction. Preferably, the rotation time can be ≥1 min, particularly preferably ≥4 min and/or ≤10 min, preferably ≤7 min.

In an advantageous embodiment of the invention, a plurality of vessels with a plurality of grinders can be provided in the device. In particular the vessels can be cavities of a microtiter plate. In this way, the tissue dissociation can be done in parallel. It is also possible to use the cavities in the microtiter plate individually, partially or in parallel. For partial use, disposable cavity strips for example are suitable, the base plate serving only as frame. The cover can serve for example as carrier of a grinding cylinder or as carrier of a plurality of grinding cylinders, e.g. also in the form of strips.

In an advantageous embodiment of the method, the cell suspension produced by actuation of the dissociation unit or of the grinder can be purified and/or centrifuged after actuation of the dissociation unit or of the grinder. For example the device here can firstly be placed on an actuation device by means of which the dissociation unit or the grinder is actuated for the tissue dissociation and then the device can be introduced into a centrifuge in order to centrifuge the dissociated cell suspension in the reagent vessel.

According to the invention at least one medium can be added to the tissue sample, before, during and/or after actuation of the dissociation unit or of the grinder. This can be effected for example by a septum, configured as described above, in an opening of the cover and/or of the closing cap.

In an advantageous embodiment of the invention, a rotation direction and/or a speed of rotation of the actuation of the dissociation unit or of the grinder can be stored based on parameters detected during the actuation. These parameters can comprise for example one or more, selected from a torque, a rheological parameter and/or an optical density. In this way, the progress of the dissociation during the course of the implementation of the method can be detected so that the tissue desintegration can be implemented in a controlled manner up to a prescribed point and, upon reaching prescribed target values of the considered parameters, can be ended.

In an advantageous embodiment, a force transmitted to the dissociation unit or the grinder by an actuator or a torque transmitted to the dissociation unit, by an actuator can be measured by means of one or more sensors. From the thus measured force or the thus measured torque, a dissociation degree of the tissue can be determined.

Advantageously, it can be checked, by means of measurement results from actuation of the dissociation unit or of the grinder, which sire determined by one or a combination of sensors. In this way, in particular the running time can be adjusted for optimisation of the dissociation degree.

In the following, the invention is intended to be explained on the basis of some Figures by way of example. The features described in the Figures can thereby be produced independently of the concrete example and be combined amongst the examples. The same reference numbers characterise the same or corresponding features.

Figure 2:
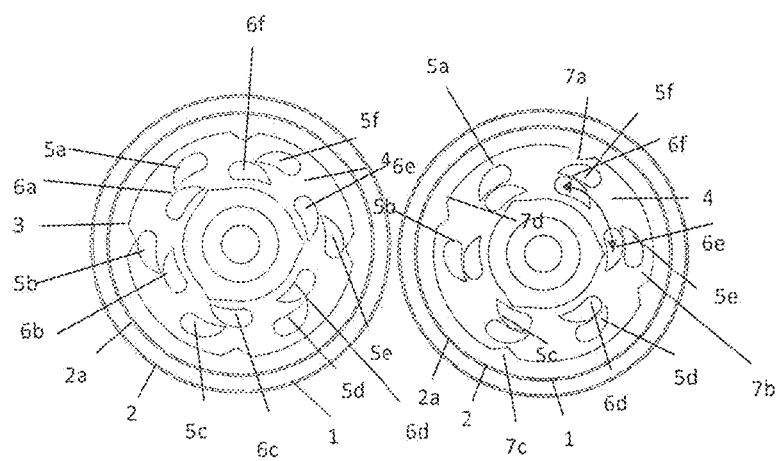
Figure 3:
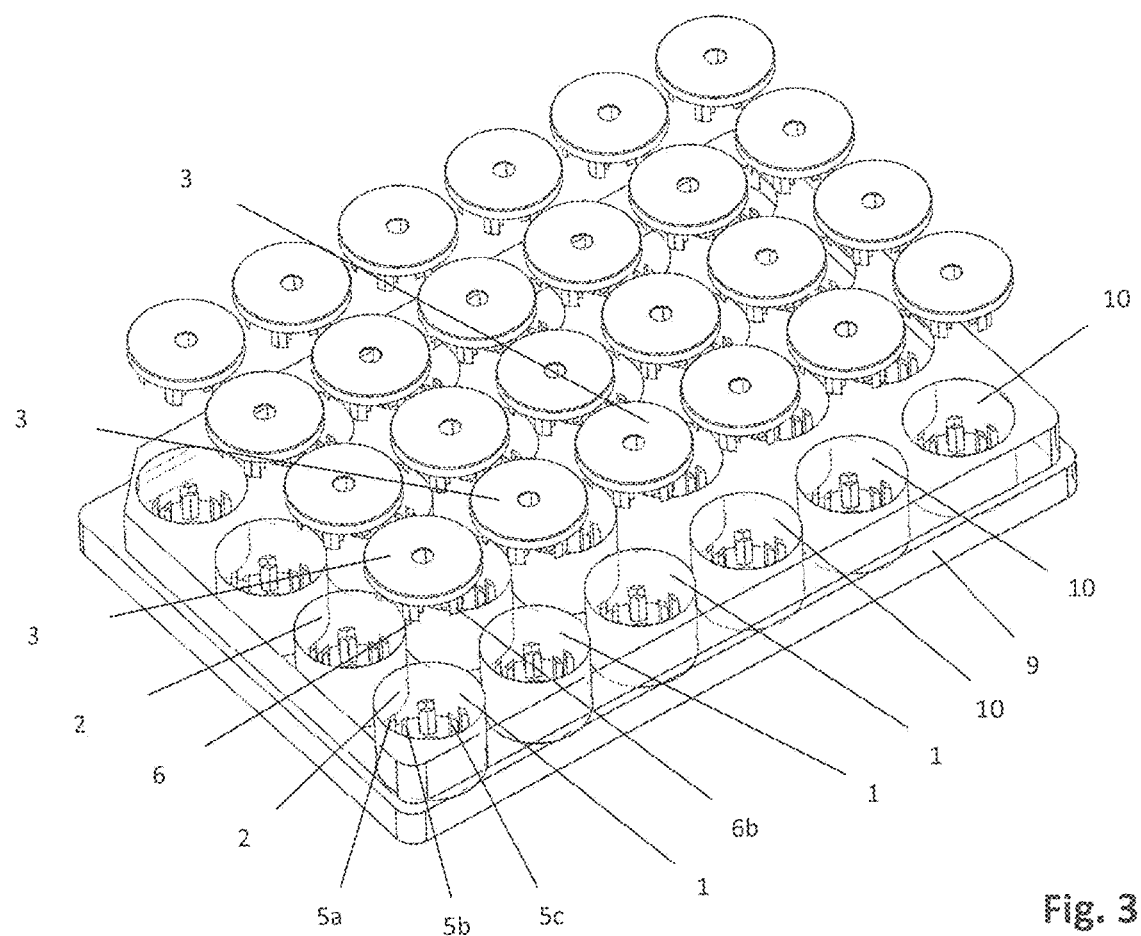
Figure 4:
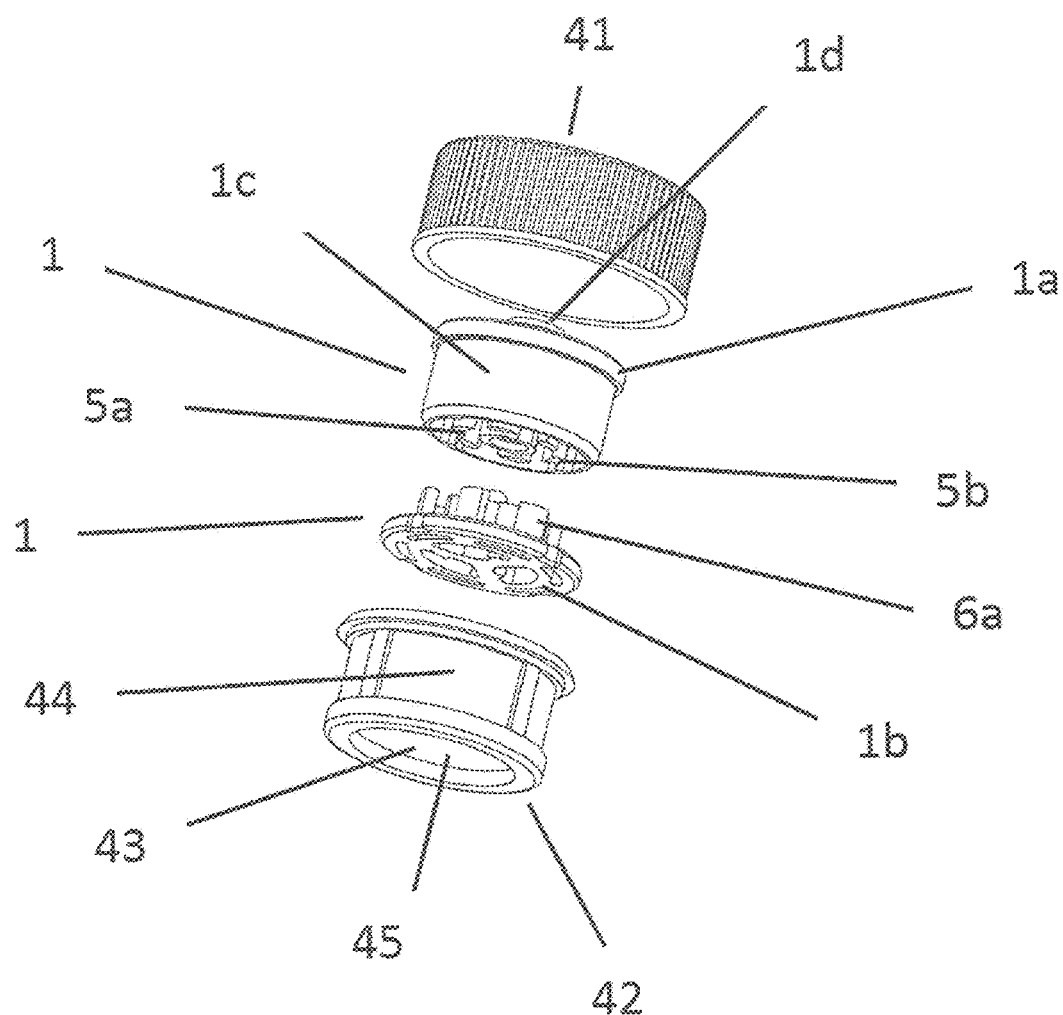
Figure 5:
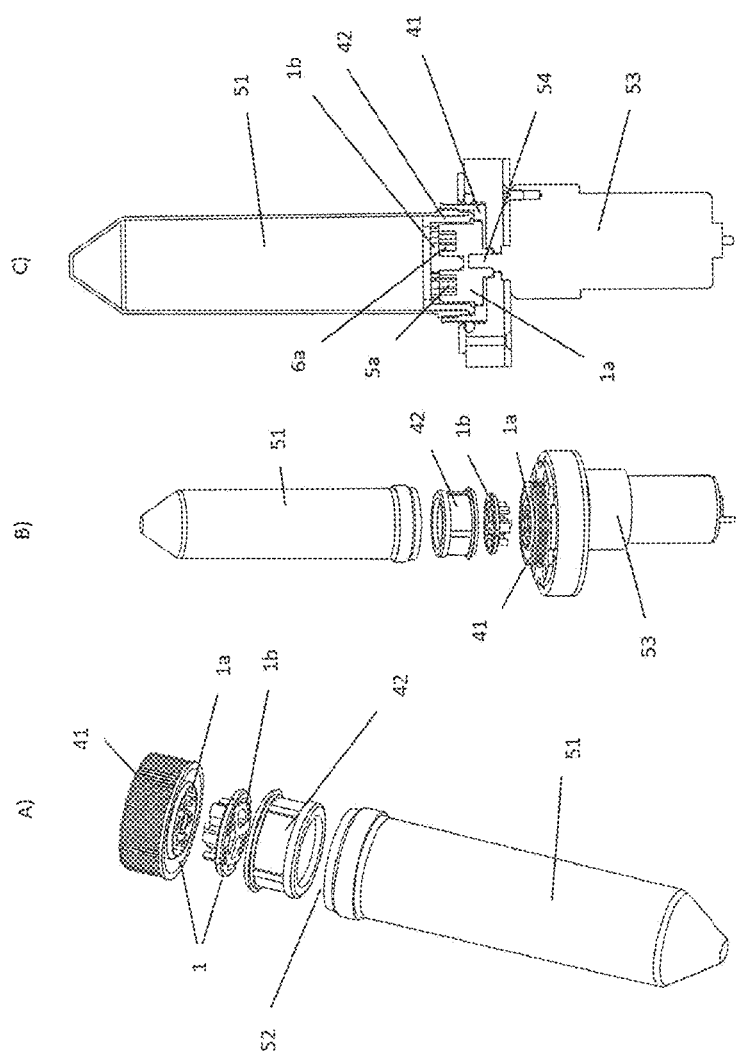
Figure 6:
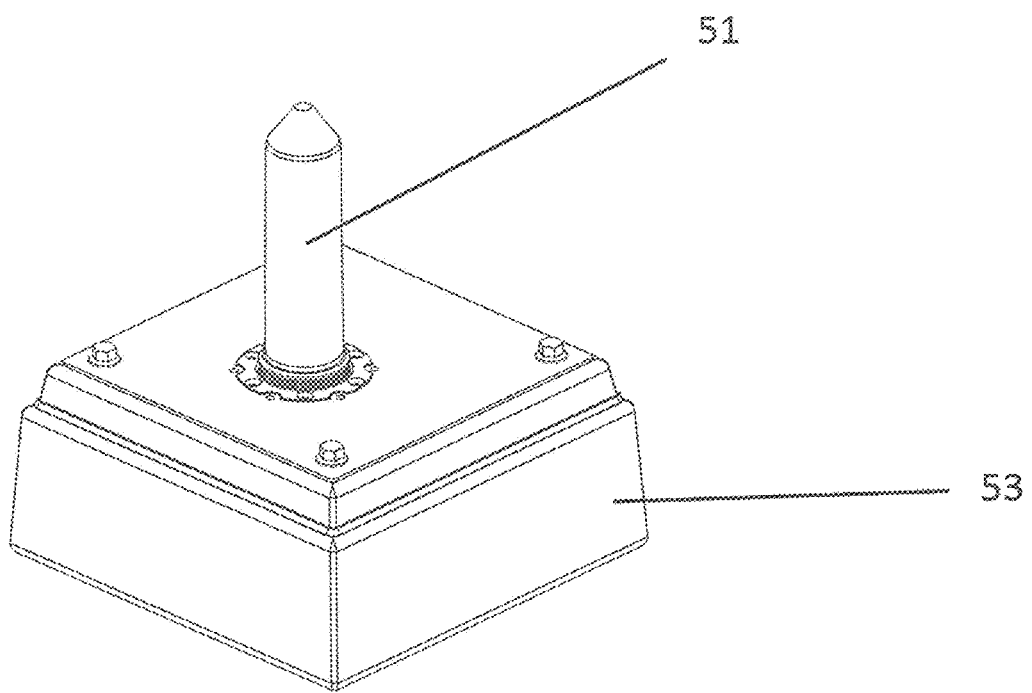

There are shown:

FIG. 1 an example of a device according to the invention for the dissociation of tissue, FIG. 2 a further example of a device according to the invention for the dissociation of tissue, FIG. 3 a large number of devices according to the invention for the dissociation of tissue, disposed in a microtiter plate, FIG. 4 a device according to the invention for the dissociation of tissue with a dissociation unit and a pot-shaped cell strainer, FIG. 5 a device as shown in FIG. 4 with a reagent vessel, and FIG. 6 the device shown in FIG. 5 placed on an actuation device for actuation of the dissociation unit.

FIG. 1 shows an example of a device according to the invention for the dissociation of tissue. In the illustrated example, the device 1 for the dissociation of tissue is configured to be circular. The device has a base 2 of which, in the plan view of FIG. 1, a circular side wall 2a can be detected. The base 2 is closed by a cover 3 of which, in the sectional image of FIG. 1, a cylindrical side wall 3 can be seen. The elements 2 and 3 together form a vessel 4 for receiving a tissue sample. The vessel 4 here is delimited by the side wall 3 of the cover. The base 2 has a base element about a centre of the housing 2 which has an opening in its interior. A central element of the cover 3 can engage in this opening.

In the example shown in FIG. 1, the device has a grinder with two mutually movable rows of teeth 5a-5f and 6a-6f. Each of the rows of teeth has a plurality of teeth 5a-5f or 6a-6f. The rows of teeth are disposed relative to each other at such a spacing that the teeth 5a-5f and 6a-6f of these respectively adjacent rows of teeth effect a dissociation of a part of the tissue sample in a spacing region by their minimum spacing relative to each other. The partial images of FIG. 1 show the grinder in a state in which the teeth 5*a* and 6*a* to 5*f* and 6*f* respectively have a minimum spacing relative to each other.

In the example shown in FIG. 1, the teeth have a drop shape in a cross-section perpendicular to the axis of rotation about which the rows of teeth rotate. In the direction of a line along which the teeth 5*a*-5*f* or 6*a*-6*f* are disposed in the corresponding row of teeth, the drop shape has, on the one hand, a tip and, on the other hand, opposite, a rounding. The tips of the teeth 5*a*-5*f* of the one row of teeth are directed in the opposite direction to the tips of the teeth 6*a*-6*f* of the other row of teeth. Likewise, the roundings of these teeth are directed in opposite directions to each other. As a result, the teeth 5*a*-5*f* together with the teeth 6*a*-6*f* cut the tissue if they move in the direction of the tips and grind the tissue if they move in the direction of the roundings.

In order to improve the dissociation result, the wall of the cover 3 has triangular projections 7*a*-7*d* which protrude from the wall in the direction of the teeth 5*a*-5*f* and 6*a*-6*f* and also in the direction of the centre of the vessel 4. If the teeth 6*a*-6*f* move past these projections 7*a*-7*d*, then tissue is ground between the projections 7*a*-7*d* and the teeth 6*a*-6*f*.

Similarly, the base element 2*b* has triangular teeth 8*a*-8*c* which protrude in the direction of the teeth 5*a*-5*f* and 6*a*-6*f* from the base 2*b*. If the teeth 5*a*-5*f* of the inner row of teeth move past these projections 8*a*-8*c*, then tissue is ground between the teeth 5*a*-5*f* and the projections 8*a*-8*c*.

The teeth 6*a*-6*f* of the inner row of teeth can be disposed on the cover 3 and be moved together with the latter. The teeth 5*a*-5*f* of the outer row of teeth are advantageously disposed on the base 2 of the vessel 4 and fixed relative to the latter. Correspondingly, the base element 2*b* with the projections 8*a*-8*c* is advantageously disposed on the underside of the vessel 4 and fixed relative to the latter. If now the cover 3 or an element disposed on the cover 3 and bearing the teeth 6*a*-6*f* is rotated, then the teeth 6*a*-6*f* move in the circle past the teeth 5*a*-5*f* and the projections 8*a*-8*c* and effect a dissociation of the tissue. At the same time, the projections 7*a*-7*d* on the cover move past the teeth 5*a*-5*f* and effect there a dissociation of the tissue.

FIG. 2 shows a further embodiment of a device according to the invention for the dissociation of tissue. The construction of the device shown in FIG. 2 corresponds to that shown in FIG. 1 so that reference should be made to the description relating to FIG. 1. In the following, only the differences from FIG. 1 are stated.

In FIG. 2, the teeth 5*a*-5*f* and 6*a*-6*f* likewise have a drop shape which is bent however, relative to the drop shape shown in FIG. 1, in the direction about the centre and the axis of rotation. As a result, these teeth 5*a*-5*f* and 6*a*-6*f* likewise have a pointed side and a round side which are connected however, in FIG. 2, differently from in FIG. 1 by curved sides. In the illustrated example, the inner side of the outer teeth 5*a*-5*f* are optionally curved parallel to the course of this row of teeth, i.e. essentially has the same radius of curvature. The outsides of the teeth 5*a*-5*f* and 6*a*-6*f* are optionally curved with a smaller radius of curvature than the row of teeth.

FIG. 3 shows a large number of devices according to the invention which are disposed in 4×6 cavities 10 of a microtiter plate 9. For each of the cavities 10, a cover 3 is provided which carries the teeth 6*a*, 6*b* of one of the rows of teeth. Above that, each cavity 10 forms a vessel 2 in which teeth 5*a*, 5*b*, 5*c* of a further row of teeth sire disposed. The arrangement of the teeth and configuration of the teeth can be achieved as shown in FIGS. 1 and 2. The teeth. 5*a*, 5*b*, 5*c* can also be configured as inserts for the cavities 10 so that they can be inserted in commercially available microtiter plates 9.

A tissue processing can take place for example as follows in the examples of FIGS. 1 to 3. 24 cavities can be provided as shown in FIG. 3. An inner diameter of the cavities can be for example 2 cm. The teeth 5*a*-5*f* can be rotated relative to the teeth 6*a*-6*f*, for example with a speed of rotation of 60-700 rpm. In the case of other scales of the cavities and of the grinder, the speed of rotation can be adapted correspondingly. The duration of the dissociation can be chosen for example between 1 and 10 min. During this time, one or more changes of direction can be undertaken. In this way, for example pieces of tissue of a mass of 50 mg to 3 g can be dissociated, A minimum spacing of the teeth of adjacent rows of teeth can be for example between 50 and 500 µm.

FIG. 4 shows, as exploded drawing, a device according to the invention for the dissociation of tissue with a dissociation unit 1 which is configured here with a cover 1*a* and a base 1*b*. The dissociation unit is disposed, in FIG. 4, at least partially in the interior of a closing cap 41 of a reagent vessel, which is shown in FIG. 5. The device has in addition a pot-shaped cell strainer 42 in which the dissociation unit 1 is disposed. The closing cap 41, the cover 1*a*, the base 1*b* and the cell strainer 42 are disposed, in FIG. 4, cylindrically and with coaxial cylindrical axes. In FIG. 4, the components are shown separated in the direction of the cylindrical axis, in the assembled state they are all situated however one in the other.

The cell strainer 42, in the illustrated example, is configured to be pot-shaped, and in fact in the form of a circular cylinder which is closed on one side. The cell strainer 42 thereby has four cell strainer surfaces 44 in the cylindrical surface. Furthermore, that end-side 43 of the cell strainer which is orientated towards the dissociation unit 1 is closed by a cell strainer surface 45, That end-side of the pot-shaped cell strainer, which is situated opposite the cell strainer surface 45, is open.

The dissociation unit has, on the one hand, the cover 1*a* and, on the other hand, the base 1*b*. The cover 1*a* thereby has an end-side which cannot be detected in the Figure, on which a plurality of teeth 5*a*, 5*b* are disposed such that they are parallel to the cylindrical axis of the cover. The teeth of the cover 1*a* are surrounded by the jacket face 1*c* which extends along an edge of the end-side of the cover on which the teeth 5*a*, 5*b* sire disposed. The jacket face 1*c* here is a cylindrical surface, the cylindrical axis of which coincides with the cylindrical axis of the dissociation unit 1 and also of the cell strainer 42.

The base 1*b* of the dissociation unit 1 has teeth 6*a* which cooperate with the teeth of the cover for the dissociation.

In the illustrated example 1*a*, the cover 1*a* has in addition a central through-opening 1*d* which extends in the centre of the end-face which cannot be detected and is surrounded by the teeth 5*a*, 5*b*. This opening 1*d* allows, on the one hand, coupling of a motor for actuation of the cover 1*a* and furthermore also the introduction of liquids into the dissociation unit 1. Advantageously, the opening can thereby have a septum at its end orientated towards the cell strainer 42. The opening 1*d* can be configured as a tubular channel which extends from the end-face of the cover 1*a* up to the end of the jacket face 1*c* of the cover.

Advantageously, the closing cap 41 also has an opening which is coaxial to the opening 1*d* and sealed relative to the opening 1*d*.

FIG. 5 shows the dissociation unit shown in FIG. 4 as an exploded drawing with a reagent vessel 51. As in FIG. 4, the dissociation unit 1 is disposed with a cover 1*a* and a base 1*b* in the closing cap 41 and is surrounded by the ceil strainer 42. With respect to these elements, reference should be made to the description relating to FIG. 4.

The reagent vessel 51 has a circular-cylindrical shape with a tapered closed end and an opening 52 in that end-face of the cylindrical shape which is situated opposite the tip. The closing cap 41 can be screwed onto the opening 52 and surrounds or encloses the opening 52. The dissociation unit 1 and the cell strainer 42, in the screwed-on state, are disposed in the closing cap 41 and in the opening 52 or shortly behind the opening 52 in the interior of the reagent vessel 51. FIG. 5A shows the device in a perspective illustration. FIG. 5B shows the device in connection with an actuation device 53 as a perspective illustration and FIG. 5C shows the device shown in FIG. 5B assembled in a sectional view.

It can be detected in FIG. 5C that the closing cap 41 is screwed or fitted on the reagent vessel 51 and thereby clamps the cell strainer 42 between an edge around the opening 52 of the reagent vessel 51 and the closing cap 41. As a result, the cell strainer 42 is retained in the opening 52 in the interior of the reagent vessel 51, directly behind the opening 52. A shaft 54 of the actuation device 53 engages in the cover 1*a* of the dissociation unit, as a result of which the latter is rotatable. The base 1*b* of the dissociation unit 1 is fixed relative to the cell strainer and the reagent vessel 51 and is not jointly rotated when rotating the cover 1*a*. As a result, the teeth 5*a* of the cover 1*a* move relative to the teeth 6*a* of the base 1*b* and thus effect a dissociation of tissue introduced into the dissociation unit 1. The cover 1*a* and the base 1*b* of the dissociation unit 1 form a housing, within which the tissue is dissociated. In the illustrated example, the housing is however not fluid-impermeable so that the cell suspension can flow out of the dissociation unit 1 if the device is rotated such that the reagent vessel 51 is pointing downwards or if the device is introduced into a centrifuge in which the centrifugal force acts in the direction of the reagent vessel 51.

The reagent vessel 51 can advantageously be a standard laboratory vessel, and also the cover 41 can be a standard laboratory vessel cover. The cover can also be fixed by means of a circumferentially situated clamping ring.

The duct of the coupling of the actuator 53 to the base 1*b* of the dissociation unit 1 can be fitted with sliding bearings in order to ensure a low-resistance rotation and simultaneous impermeability.

FIG. 6 shows the device shown in FIG. 5, fitted on a tissue grinder device which acts here as actuation device 53. The tissue grinder device 53 can hereby have in turn a shaft 54 which engages in the cover 1*a* of the dissociation unit 1 and can rotate the latter.

In the following, a course of a method according to the invention is intended to be described by way of example, in which the described device can be used.

In a first step of the tissue processing, a tissue sample to be examined is introduced into the dissociation unit 1 or the housing of the dissociation unit 1. For this purpose, the cover 1*a* can be filled with the tissue and a liquid, e.g. medium or enzyme solution, and be brought together with the base 1*b* in the cell strainer 42 via a coupling ring or closing cap 41. By rotation, preferably in both directions, and optionally linear up and down movement of the dissociation unit 1, now the tissue is processed by cutting and/or grinding processes. Optionally, the cutting unit can be operated also uncoupled from the cover 1*a*, e.g. by an integrated magnet. In this case, the cover 1*a* and the dissociation unit 1 can be uncoupled and the cover 1*a* can be actuated by rotation of a magnet above the cover.

During the desintegration process, the cover 1*a* of the cutting unit is connected to the actuator 53, and is actuated by the latter. The base 1*b* of the dissociation unit 1 or of the housing 1 is stationary here and can be inserted directly into the cell strainer 42. In order to produce a closed system, the base 1*b* of the dissociation unit 1, which can be integrated in the cell strainer 42, is screwed with the cover 1*a* of the dissociation unit 1 by the closing cap 41 on the reagent vessel 51.

After ending the desintegration process, the cell suspension is separated from the tissue residues, for example by means of centrifugation. Further washing steps to increase the cell output can be effected through a septum which can be integrated in the opening 1*d* in the cover 1*b*. In the reagent vessel 51, the cell suspension can be collected and hence can remain in a closed system from introducing the tissue sample via the desintegration until continuing analysis, which reduces the danger of contamination significantly and simultaneously increases the user friendliness.

The tissue processing with the described rows of teeth can be effected, during use for centrifugal tubes 51 and cell filters (with for example a mesh width between 10 and 200 μm) with a cutting unit inner diameter of for example 2 cm and a speed of rotation of for example 10 to 700 rpm. Other scales are possible, then the speed of rotation being adapted preferably. According to the type of tissue, a rotation time of for example 1 to 10 minutes and one or more changes in direction of rotation can be sensible. With suitable adaptation of the size of the housing, a dissociation of tissue pieces from a mass of e.g. 50 mg to 3 g is achievable. The minimum spacing between teeth of adjacent rows of teeth is preferably between 50 and 500 μm.

A reagent vessel 51 is suitable for the processing of a tissue sample or a plurality of tissue samples at the same time. Advantageously, seals, e.g. in the form of sliding bearings, can be provided in order to ensure a lower-resistance rotation and simultaneous impermeability. In particular the opening in the closing cap 41 and in the cover 1*a* can hereby be sealed relative to each other. By providing the cell filter 42, tissue residues of individual cells in the closed system can be separated.

It is particularly advantageous if the breakdown degree, i.e. the dissociation efficiency, is effected via an online process control. The breakdown of the tissue sample can thereby be effected by means of sensors, e.g. by means of a measurement of turbidity, via an optical sensor and/or a torque measurement and/or rheological measurements of the breakdown tools. The received parameters can be analysed and converted into a generally valid differential equation for describing the viability and yield of the target cells with different process parameters. On the basis of the online process control, an intelligent control of the direction of rotation and speed of rotation of the grinder and also of the duration of the tissue dissociation can be effected. As a result, any tissue sample can be processed individually in order to ensure an optimum cell yield.

The method according to the invention can be effected for example by firstly the dissociation unit 1 being loaded with a tissue sample and the weight of the tissue sample being determined. In addition, medium can be added. For the dissociation, the direction of rotation, speed of rotation and/or duration of the dissociation can be controlled by the online detection of process parameters, such as torque, and rheological parameters and optical density. The received parameters can be analysed and transferred by means of degradation equations to a feedback system of the motor control of the actuator 53. The feedback system can allow an individual dissociation of each tissue sample in order to increase the efficiency and yield.

Purification of the generated cell suspension is possible. For this purpose, the reagent vessel 51 can be placed in a centrifuge. After a first centrifugation, an arbitrary number of washing steps, for example by renewed addition of medium via the integrated septum in the motor coupling, can be effected. The purified cells then collect on the base of the reagent vessel 51.

The device according to the invention and the method according to the invention allow a very specific dissociation of tissue with which a desired end state of the dissociation can be achieved very precisely. By suitable combination of geometries of the teeth, if necessary cell strainers and dissociation units and intelligent control, prescribed dissociation degrees can be adjusted precisely. The described combination of tissue dissociation and centrifugation in a closed system allows complete processing of a tissue sample without the danger of contamination. By means of the described drop shapes and bent shapes of the teeth, the tissue can be cut and/or ground in a particularly sparing manner, a choice being able to be made between cutting and grinding according to requirements. By control of the direction of rotation, the predominant force effect can be determined. In comparison to processes according to the state of the art, tissue samples are processed not only in a more sparing manner for the cells but also in a time-saving manner. The tissue need no longer be cut with a scalpel into very small pieces but rather can be processed as a whole or in a few pieces. By integration of a cell strainer, the tissue sample can be purified directly without further pipetting steps. The process is partially automatable, as a result of which a higher reproducibility and standardisation is provided. The technology can be included in automated processes.

A further advantage of the system is the ability to operate in parallel. Because of the possibility of the simultaneous use of a plurality of centrifugal tubes, the tissue processing can be achieved in parallel so that a plurality of samples can be processed at the same time. The advantage resides, on the one hand, in the time saving, on the other hand, sources of error are minimised. During the processing of a plurality of samples, all the necessary preparatory operating steps can thus be implemented simultaneously for all samples and need no longer be integrated. An improved comparability of the results is thus provided. An example of this is a specific incubation time with an enzyme solution which can be maintained only when samples are mixed with the enzyme precisely this time before the dissociation.

Because of the centrifugal tube format, the system can be integrated in an automated process. Automation prevents differences in the processing as would be the case when implemented by different colleagues. This leads to an improved reproduction and comparability of the results.

Since the device, in the centrifugal tube variant thereof, concerns disposable articles, the contamination probability and auxiliaries expenditure can be minimised very greatly.

The device is suitable both for cell breakdown and for generation of single cells made from tissue.

A cell breakdown precedes for example a protein isolation or nucleic acid isolation and also other processes which include an analysis of cell components.

The more sparing dissociation of tissue is advantageous when single cells are required. This is for example the case when testing tumour cells with mass spectrometry, infrared spectroscopy or ELISA. Potential tumour tissue can be dissociated for histological tests. In addition, the production of single-cell suspensions is important for generation of 2D-cultures, 3D-cultures, single-cell characterisation, high-throughput drug screening and organ-on-chip technology. The system is not restricted to use on tumour tissue but rather can be adapted theoretically to any type of tissue.

The invention claimed is:

1. A device for dissociation of tissue, the device comprising:
   at least one dissociation unit for receiving a tissue sample; and
   at least one cell strainer, wherein the at least one dissociation unit is disposed at least partially in the at least one cell strainer, and wherein the at least one dissociation unit includes:
      at least one vessel for receiving the tissue sample; and
      a grinder disposed in the at least one vessel, wherein the grinder includes at least one first row of teeth with a plurality of teeth and at least one second row of teeth with a second plurality of teeth, the at least one first row of teeth being disposed on a base of the at least one vessel and the at least one second row of teeth being disposed on a cover of the at least one vessel, the at least one first row of teeth being movable relative to the at least one second row of teeth so that the teeth of the at least one first row of teeth move past the teeth of the at least one second row of teeth, wherein one of the at least one first row of teeth and one of the at least one second row of teeth are disposed at such a spacing respectively adjacent to each other so that the teeth of the respectively adjacent rows of teeth, when they are moved past with respect to each other, effect a dissociation of a part of the tissue sample in a spacing region by their minimum spacing relative to each other.

2. The device according to claim 1, wherein the teeth are configured such that, when the respectively adjacent rows of teeth move past each other in a first direction, they cut at least a part of the tissue sample, and when the respectively adjacent rows of teeth move past each other in a second direction opposite to the first direction, they grind at least a part of the tissue sample.

3. The device according to claim 1, further comprising:
   a reagent vessel, wherein the at least one cell strainer and the at least one dissociation unit are disposed in an opening of the reagent vessel.

4. The device according to claim 2, wherein the at least one second row of teeth disposed in the cover of the at least one vessel are movable relative to the reagent vessel and the at least one first row of teeth disposed in the base of the at least one vessel are fixed relative to the reagent vessel.

5. The device according to claim 1, wherein the respectively adjacent rows of teeth extend circularly and concentrically to each other.

6. The device according to claim 1, further comprising:
   a side wall delimiting the at least one vessel having one or more projections in a direction of the at least one first row of teeth or the at least one second row of teeth, wherein a of teeth situated closest to the side wall is spaced from the side wall so that the teeth of the row of teeth situated closest to the side wall effect a dissociation of a part of the tissue sample in a spacing region by a minimum spacing from the one or more projections.

7. The device according to claim 1, the at least one vessel includes a base element surrounded by at least one of the first row of teeth or the second row of teeth, wherein the base element includes one or more projections in a direction of the first row of teeth or the second row of teeth, wherein a row of teeth closest to the base element is spaced from the base element such that the teeth of the row of teeth closest to the base element effect a dissociation of a part of the tissue sample in a spacing region by a minimum spacing from the one or more projections.

8. The device according to claim 1, wherein a diameter of the at least one vessel, in that plane in which the rows of teeth extend, is greater than or equal to 0.5 cm, and/or less than or equal to 4 cm.

9. The device according to claim 1, wherein a minimum spacing of teeth of adjacent ones of the at least one first row of teeth and the at least one second row of teeth are greater than or equal to 50 μm and/or less than or equal to 500 μm.

10. The device according to claim 1, a first half of the respectively adjacent rows of teeth are disposed on the cover of the at least one vessel and a second half of the respectively adjacent rows of teeth are disposed on the base of the at least one vessel, wherein the first half of the respectively adjacent rows of teeth disposed on the cover are adjacent to the second half of the respectively adjacent rows of teeth disposed on the base in a plane in which the respectively adjacent rows of teeth extend.

11. The device according to claim 10, the first half of the respectively adjacent rows of teeth disposed on the cover are movable relative to the cover.

12. The device according to claim 1, wherein the cover of the vessel includes a magnetic element, the magnetic cover element allowing the cover to actuate for moving the at least one second row of teeth respective to the at least one first row of teeth.

13. The device according to claim 1, wherein at least one of the at least one cell strainer or the base include one or more webs, for preventing a relative movement of the base relative to the at least one cell strainer.

14. A device for dissociation of tissue, comprising:
at least one vessel for receiving a tissue sample; and
a grinder disposed in the at least one vessel, wherein the grinder includes at least two mutually movable rows of teeth, wherein each of the at least two mutually movable rows of teeth include a plurality of teeth, wherein adjacent ones of the at least two mutually movable rows of teeth being disposed at such a spacing relative to each other that the teeth of these respectively adjacent rows of teeth effect a dissociation of a part of the tissue sample in a spacing region by their minimum spacing relative to each other, wherein the respectively adjacent rows of teeth are configured such that, when they move past each other in a first direction, the respectively adjacent rows of teeth cut at least part of the tissue sample and, when the respectively adjacent rows of teeth move past each other in a second direction opposite to the first direction, grind at least part of the tissue sample, wherein the respectively adjacent rows of teeth extend in a common plane and are mutually movable in the common plane, wherein the teeth of the respectively adjacent rows of teeth have a cross-section parallel to the common plane, which has a pointed corner and a rounded or blunt side situated opposite the pointed corner, and wherein the pointed corners of teeth of the respectively adjacent rows of teeth are directed in opposite directions.

15. The device according to claim 14, further comprising:
a reagent vessel, wherein the at least one vessel and the grinder are disposed in an opening of the reagent vessel, wherein one row of the respectively adjacent rows of teeth are disposed in a cover of the at least one vessel and are movable relative to the reagent vessel, and wherein the other row of the respectively adjacent rows of teeth are disposed in a base of the at least one vessel and are fixed relative to the reagent vessel.

16. The device according to claim 15, wherein at least one of a cell strainer and a dissociation unit or the at least one vessel and the grinder are disposed at least partially inside a closing cap of the reagent vessel, and wherein the closing cap surround the opening of the reagent vessel.

17. The device according to claim 16, wherein the closing cap includes an opening located in a center of the closing cap, wherein the cover of the at least one vessel includes an opening coaxial to the opening of the closing cap, and wherein the opening in the closing cap and the opening in the cover are configured such that a driveshaft actuates the cover of the vessel for moving the teeth of the at least one second row of teeth relative to the teeth of the at least one first row of teeth.

18. The device according to claim 17, wherein the opening in the cover is impermeable relative to the opening in the closing cap.

19. The device according to claim 16, further comprising:
a septum disposed in at least one of the opening in the closing cap or in the opening in the cover of the at least one vessel, through which liquid is introduced into at least one of the at least one vessel or the reagent vessel.

20. The device according to claim 14, wherein an edge of the cross-section connects a tip to the rounded side is curved in a direction of a line along which the row of teeth, to which a corresponding tooth belongs, extends.

21. A method for dissociation of tissue, the method comprising:
introducing a tissue sample being into a device, the device comprising:
at least one dissociation unit for receiving the tissue sample; and
at least one cell strainer, wherein the at least one dissociation unit is disposed at least partially in the at least one cell strainer;
at least one vessel for receiving the tissue sample; and
at least one grinder disposed in the at least one vessel, wherein the at least one grinder includes a first row of teeth, the first row of teeth including a first plurality of teeth, and a second row of teeth, the second row of teeth including a second plurality of teeth, wherein the first row of teeth is located on a base of the at least one vessel and the second row of teeth are located on a cover of the at least one vessel, wherein the first row of teeth is movable relative to the second row of teeth so that the teeth of the first row of teeth move past the teeth of the second row of teeth, wherein the first row of teeth and the second row of teeth are spaced respectively adjacent to each other so that the teeth of the first row of teeth and the teeth of the second row of teeth, when they are moved past each other, effect a dissociation of a part of the tissue sample in a spacing region representing a minimum spacing of the first row of teeth and the second row of teeth relative to each other; and
actuating at least one of the dissociation unit or the grinder.

22. The method according to claim 21, wherein the first row of teeth and the second row of teeth are circular and movable relative to each other at a speed of rotation of greater than or equal to 60 rpm and/or less than or equal to 700 rpm.

23. The method according to claim 21, further comprising:
   after actuation of the dissociation unit or of the grinder, producing a cell suspension by actuation of the dissociation unit or of the grinder being purified.

24. The method according to claim 23, wherein the cell suspension is centrifuged in a reaction vessel, wherein at least one of the dissociation unit or the grinder is disposed in an opening of the reaction vessel.

25. The method according to claim 21, further comprising:
   adding at least one medium being to the tissue sample, before, during and/or after actuation of the dissociation unit or of the grinder.

26. The method according to claim 21, wherein a direction of rotation and/or a speed of rotation of the actuation of the dissociation unit or of the grinder are controlled based on parameters detected during the actuation, wherein the parameters include one or more of a torque, a rheological parameter, or an optical density.

27. The method according to claim 21, wherein a force transmitted to the dissociation unit or to the grinder is measured using one or more sensors, and wherein a dissociation degree of the tissue determined based on the measured force.

28. The method according to claim 21, wherein while the first row of teeth and the second row of teeth are moved relative to each other are moved periodically relative to each other in a direction perpendicular to the direction of the movement.

* * * * *